United States Patent [19]

Moilliet et al.

[11] Patent Number: 5,279,714
[45] Date of Patent: Jan. 18, 1994

[54] PREPARATION OF FLUOROANILINES BY ELECTROCHEMICAL MEANS

[75] Inventors: John S. Moilliet, Bury; Ian K. Jones, Burnage, both of England

[73] Assignee: Imperial Chemical Industries PLC, London, England

[21] Appl. No.: 853,298

[22] Filed: Mar. 18, 1992

[30] Foreign Application Priority Data

Mar. 22, 1991 [GB] United Kingdom ............... 9106134

[51] Int. Cl.$^5$ ............................................. C25B 3/00
[52] U.S. Cl. ................................... 204/59 F; 204/74; 204/81; 564/416; 564/417; 564/420
[58] Field of Search ............... 204/59; 564/416, 417, 564/420

[56] References Cited

U.S. PATENT DOCUMENTS

| | | | |
|---|---|---|---|
| 3,511,761 | 5/1970 | Childs et al. | 204/59 |
| 3,910,985 | 10/1975 | Montijn et al. | 564/417 |
| 4,592,810 | 6/1986 | Bon et al. | 204/59 R |

FOREIGN PATENT DOCUMENTS

| | | | |
|---|---|---|---|
| 0313160 | 4/1989 | European Pat. Off. | |
| 1257184 | 12/1971 | United Kingdom | 204/59 F |
| 2191480 | 12/1987 | United Kingdom | |

*Primary Examiner*—John Niebling
*Assistant Examiner*—C. Delacroix-Muirheid
*Attorney, Agent, or Firm*—Cushman, Darby & Cushman

[57] ABSTRACT

A process for the preparation of a compound of Formula A:

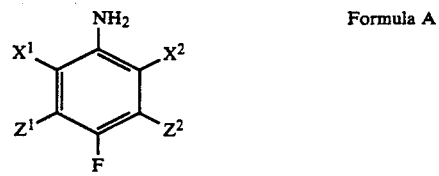

Formula A wherein
$X^1$ and $X^2$ are independently selected from H or any substituent which does not interfere with the electrochemical reductive fluorination; and
$Z^1$ and $Z^2$ are each independently selected from H or an electron donating group;
which comprises electrochemical reductive fluorination of a compound of Formula B:

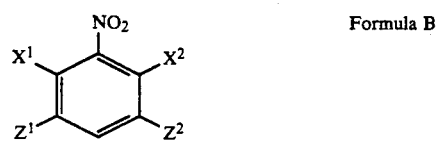

Formula B wherein $X^1$, $X^2$, $Z^1$ and $Z^2$ are as defined above in a mixture of anhydrous hydrogen fluoride and an alkali metal fluoride.

The 4-fluoroanilines find use as intermediates in the manufacture of a wide range of agrochemicals, dyestuffs and pharmaceuticals.

7 Claims, No Drawings

PREPARATION OF FLUOROANILINES BY ELECTROCHEMICAL MEANS

This invention relates to a process for the preparation of a fluoroaniline by simultaneous electrochemical reduction and ring fluorination (electrochemical reductive fluorination) of a nitrobenzene.

The preparation of a mixture of 2- and 4-chloroanilines from nitrobenzene by electrochemical reduction in aqueous hydrochloric acid solution in a divided cell is disclosed in Berichte 29, 1894 (1896). This reaction is accompanied by formation of p-aminophenol which is an undesirable by product. The preparation of certain 4-chloroanilines by electrochemical reduction of the corresponding nitrobenzenes in a mixture of hydrochloric acid and an alcohol is disclosed in Z.Electrochim. 7, 590 (1902).

Attempts to prepare 4-fluoroanilines using an electrochemical reduction of nitrobenzene in aqueous hydrofluoric acid fail because of the highly corrosive nature of the acid which rapidly destroys the electrodes and thus prevents electric current passing through the cell. Use of anhydrous hydrogen fluoride as the reduction medium also fails to give the desired product.

Surprisingly, we have now found that nitrobenzenes may be reduced and simultaneously substituted with fluorine exclusively at the 4-position relative to the nitro group to form the corresponding 4-fluoroanilines by an electrochemical process using a composite reaction medium.

According to the present invention there is provided a process for the preparation of a compound of Formula A:

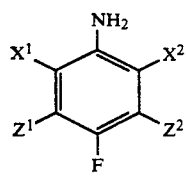

Formula A wherein
$X^1$ and $X^2$ are independently selected from H or any substituent which does not interfere with the electrochemical reductive fluorination; and
$Z^1$ and $Z^2$ are each independently selected from H or an electron donating group;
which comprises electrochemical reductive fluorination of a compound of Formula B:

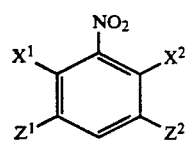

Formula B wherein $X^1$, $X^2$, $Z^1$ and $Z^2$ are as defined above in a mixture of anhydrous hydrogen fluoride and an alkali metal fluoride. Where $X^1$ or $X^2$ is a substituent, this may be an electron withdrawing group or an electron donating group.

It is preferred that one of $X^1$ and $X^2$ is an electron withdrawing group or hydrogen and the other of $X^1$ and $X^2$ is H, an electron withdrawing group or any electron donating group.

When either of $X^1$ and $X^2$ is an electron withdrawing group, this is preferably selected from halogen, —$CF_3$, —COOH, —CN. It is especially preferred that the electron withdrawing group represented by $X^1$ or $X^2$ is —F or —Cl.

When either of $X^1$ and $X^2$ is an electron donating group it is preferred that this is unbranched or branched $C_{1-6}$-alkyl. Where $X^1$ or $X^2$ is an electron donating group this is preferably —$CH_3$.

It is preferred that $Z^1$ and $Z^2$ are each independently hydrogen or unbranched or branched $C_{1-6}$-alkyl. It is especially preferred that $Z^1$ and $Z^2$ are each independently —H or —$CH_3$.

Examples of fluoroanilines which may be prepared by the process of the invention include:
4-fluoroaniline
2,4-difluoroaniline
2-chloro-4-fluoroaniline
2-bromo-4-fluoroaniline
2,4,6-trifluoroaniline
2-chloro-4,6-difluoroaniline
3-methyl-4-fluoroaniline
3,5-dimethyl-4-fluoroaniline
2-fluoro-3-methyl-4-fluoroaniline
2-chloro-3-methyl-4-fluoroaniline
2-fluoro-3,5-dimethyl-4-fluoroaniline
2-chloro-3,5-dimethyl-4-fluoroaniline
and examples of nitrobenzenes from which they may be prepared include: nitrobenzene
2-fluoronitrobenzene
2-chloronitrobenzene
2-bromonitrobenzene
2,6-difluoronitrobenzene
2-chloro-6-fluoronitrobenzene
3-methylnitrobenzene
3,5-dimethylnitrobenzene
2-fluoro-3-methylnitrobenzene
2-chloro-3-methylnitrobenzene
2-fluror-3,5-dimethylnitrobenzene
2-chloro-3,5-dimethylnitrobenzene.

The process is preferably performed by passing an electric current through a divided electrochemical cell. A suitable divided electrochemical cell comprises two chambers an anode chamber and a cathode chamber each fitted with an electrode and separated by a porous membrane which allows selective permeation of protons. Suitable membranes include cation exchange membranes such as "NAFION" perfluorinated membranes (Du Pont, NAFION is a trade mark). In operation, a mixture of an alkali metal fluoride in hydrogen fluoride is placed in each chamber and a compound of Formula B is placed in the cathode chamber. In order to promote reaction, the cathode chamber may also contain aids to solubilise the compound of Formula B in the reaction medium such as organic liquids. Suitable organic liquids are those which are miscible with, but are not reactive towards, hydrogen fluoride. Preferred organic liquids are ethers, especially methoxyethane, 1,2-dimethoxyethane, diethyleneglycol dimethylether and tetrahydrofuran.

The alkali metal fluoride is preferably selected from lithium, sodium and potassium fluorides and more especially is potassium fluoride.

It is preferred that the hydrogen fluoride is substantially anhydrous, but it may contain a small amount of water provided small amounts of by-products can be tolerated. It is preferred that the water content of the hydrogen fluoride is less than 2%, more preferably less than 1% and especially less than 0.2%. To minimise the formation of by-products caused by the presence of water, a dehydrating agent may be added to the anode and/or cathode chambers. Suitable dehydrating agents are those which do not react with hydrogen fluoride or the compound of Formula B or the derived compound of Formula A. Preferred dehydrating agents are those which chemically bond water by reacting with it such as phosphorus pentoxide and acyl halides.

The concentration of alkali metal fluoride in hydrogen fluoride in each chamber of the divided electrochemical cell may be varied within wide limits and convenient ranges are from 1 part to 50 parts by weight, preferably is from 5 parts to 25 parts and especially from 10 parts to 20 parts of alkali-metal fluoride in 100 parts hydrogen fluoride.

The concentration of the compound of Formula B in the cathode solution may be varied between wide limits. These limits depend on the identity of the compound of Formula B, its solubility in hydrogen fluoride, the nature of any organic liquid present, and the temperature. It is not essential that the compound of Formula B is completely dissolved in the cathode solution but solubility, at least 0.5 parts of the compound of Formula B in 100 parts of the cathode medium, is preferable to give a reasonable rate of electrochemical reductive fluorination. The amount of compound of Formula B is conveniently from 1 part to 50 parts, preferably from 1 part to 10 parts by weight of compound of the Formula B in 100 parts of cathode solution.

The electrochemical reductive fluorination may be carried out at any temperature up to 40° C., but preferably at from 15° C. to 20° C.

The electrodes in the divided electrochemical cell may be constructed from a metal such as nickel or titanium, from carbon or from other hydrogen fluoride resistant materials such as titanium oxide ceramics, for example EBONEX (Ebonex Technology Inc.; EBONEX is a trade mark). The anode and cathode may be of different materials for example the anode may be carbon and the cathode nickel, or the anode may be nickel and the cathode carbon. It is preferred that when the anode is carbon the cathode is carbon or nickel and that when the anode is nickel the cathode is carbon. It is further preferred that carbon electrodes are of the glassy carbon type (available from Le Carbone, Port Slade, Surrey).

The current passed through the divided electrochemical cell may be varied within wide limits and is typically from 100 mA to 1500 mA, preferably from 300 mA to 1200 mA and especially from 500 mA to 700 mA.

The electrochemical reductive fluorination may be continued until substantially all of the compound of Formula B has been converted or the electrochemical reductive fluorination may be continued to partial completion for example until approximately 25 to 45% conversion before the desired product is removed and starting materials are recycled, this improves the yield of the desired 4-fluoroaniline derivative and reduces the formation of by-products.

When the reaction has reached the desired conversion the product may be isolated and recyclable starting materials recovered in any convenient manner. For example the reaction mixture may be cooled, the amine product present in the hydrogen fluoride as the amine hydrofluoride, extracted with water, the aqueous solution of product neutralised with ice cold ammonia solution and the product recovered by steam distillation.

The recyclable starting materials left after the extraction may be re-used directly or they may be purified by steam or dry distillation before re-use.

Alternatively, the product may be isolated by distilling the hydrogen fluoride from the reaction mixture, neutralising the residual material and recovering the product by steam distillation. The steam distillate contains the desired 4-fluoroaniline derivative which may be purified by any convenient means; for example, by partial neutralisation and extraction into any suitable water immiscible solvent, by crystallisation or by fractional distillation.

The 4-fluoroanilines prepared by the present invention find use as intermediates in the manufacture of a wide range of agrochemicals, dyestuffs and pharmaceuticals.

The invention is illustrated by the following examples.

EXAMPLE 1

A divided electrochemical cell consisting of two chambers separated by a cation exchange membrane (NAFION membrane, Du Pont) was fitted with a carbon anode (5 cm$^2$, Le Carbone, Port Slade, Surrey) and a nickel cathode (5 cm$^2$ cut from 3 mm thick Nickel Sheet, Koch Light, Hatfield, Hertfordshire). The anode chamber was filled with a solution of 15 parts of potassium fluoride in 100 parts of anhydrous hydrogen fluoride. The cathode chamber was filled with a solution containing 15 parts of potassium fluoride and 3 parts of 2-fluoronitrobenzene in 100 parts of anhydrous hydrogen fluoride.

A current of 600 mA was passed through the electrochemical cell until 99% of the nitrobenzene had been consumed (% conversion of nitro). A 2.3:1 mixture of 1.9 parts 2,4-difluoroaniline (2,4-DFA) and 0.83 parts 2-fluoroaniline (2-FA) representing a 69% yield of the desired 2,4-DFA was obtained.

EXAMPLES 2-5

The following Examples used the same procedure as in Example 1 but different combinations of electrode were used and the total conversion of the nitrobenzene compound was varied. The variables and yields are summarised in Table 1 below:

TABLE 1

| Example | Anode | Cathode | % Conversion of Nitro | Ratio DFA:2FA | % DFA |
|---------|-------|---------|----------------------|---------------|-------|
| 2 | Ni | C | 56 | 9.0:1 | 49 |
| 3 | Ni | C | 91 | 4.1:1 | 73 |
| 4 | Ni | Ni | 99 | 2.3:1 | 67 |
| 5 | C | C | 99 | 5.06:1 | 65 |

DFA = 2,4-difluoroaniline
2FA = 2-fluoroaniline

EXAMPLE 6

A divided electrochemical cell as in Example 1 was fitted with a Dimensionally Stable Electrode (DSE from ICI Chemicals and Polymers) anode and a nickel cathode as in Example 1. The anode chamber was filled with saturated aqueous potassium chloride solution. The cathode chamber was filled with a solution of 15 parts potassium fluoride in 100 parts of anhydrous hydrogen fluoride and 3 parts of 2-fluoronitrobenzene were added. A current of 600 mA was passed through the electrochemical cell until 99% of the nitrobenzene had been consumed. A 1.09:1 mixture of 2,4-DFA and 2-FA representing a 50% yield of 2,4-DFA was obtained.

EXAMPLE 7

The procedure of Example 2 was followed except that 1.5 parts of phosphorus pentoxide was added to both the anode and cathode solution. A 3.66:1 mixture of 2,4-DFA and 2-FA representing a 62% yield of 2,4-DFA was obtained.

EXAMPLE 8

The procedure of Example 7 was followed except that the cathode was nickel. A 2.05:1 mixture of 2,4-DFA and 2-FA representing a 60% yield of 2,4-DFA was obtained.

EXAMPLE 9

The procedure of Example 7 was followed except that the anode was carbon and the cathode was nickel. A 2.26:1 mixture of 2,4-DFA and 2-FA representing a 65% yield of 2,4-DFA was obtained.

EXAMPLE 10

The procedure of Example 2 was followed except that the reaction was taken to 99% conversion of nitro. A 5.33:1 mixture of 2,4-DFA and 2-FA representing a 60% yield of 2,4-DFA was obtained.

EXAMPLE 11

The procedure of Example 10 was followed except that the a current of 1200 mA was passed through the electrochemical cell. A 1.64:1 mixture of 2,4-DFA and 2-FA representing a 65% yield of 2,4-DFA was obtained.

EXAMPLE 12

The procedure of Example 10 was followed except that the a current of 300 mA was passed through the electrochemical cell. A 5.29:1 mixture of 2,4-DFA and 2-FA representing a 65% yield of 2,4-DFA was obtained.

We claim:

1. A process for the preparation of a compound of Formula A:

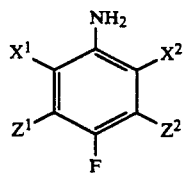

Formula A which comprises electrochemical reductive fluorination of a compound of Formula B:

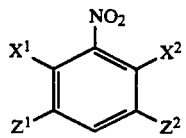

Formula B in a mixture of anhydrous hydrogen fluoride and an alkali metal fluoride, wherein
  $X^1$ and $X^2$ are independently selected from H or any substituent which does not interfere with the electrochemical reductive fluorination; and
  $Z^1$ and $Z^2$ are each independently selected from H or an electron donating group.

2. A process according to claim 1, wherein the compound of Formula A $X^1$ and $X^2$ are each independently selected from the group consisting of —H, halogen, —$CF_3$, —COOH, CN, branched $C_1$-$C_6$ alkyl and unbranched $C_{1-6}$-alkyl, and $Z^1$ and $Z^2$ are each independently —H, branched $C_1$-$C_6$ alkyl or unbranched $C_{1-6}$-alkyl.

3. A process according to claim 1 or 2 wherein the compound of Formula A $X^1$ and $X^2$ are each independently —H, —$CH_3$, —F or —Cl, and $Z^1$ and $Z^2$ are each independently —H or —$CH_3$.

4. A process according to claim 1 or 2 wherein the electrochemical reductive fluorination is performed by passing an electric current through a divided electrochemical cell comprising two chambers each of which is fitted with an electrode.

5. A process according to claim 4, wherein a current of 100 mA to 1500 mA is passed through the divided electrochemical cell.

6. A process according to claim 4 wherein each electrode is independently carbon or nickel.

7. A process according to claim 5, wherein each electrode is independently carbon or nickel.

* * * * *